United States Patent
Hancock et al.

(10) Patent No.: US 11,950,825 B2
(45) Date of Patent: Apr. 9, 2024

(54) APPARATUS FOR TREATING URINARY TRACT INFECTIONS

(71) Applicant: CREO MEDICAL LIMITED, Chepstow (GB)

(72) Inventors: Christopher Paul Hancock, Bath (GB); Morgan Bryant, Chepstow (GB); Louis Turner, Chepstow (GB); Sandra Swain, Chepstow (GB); Julian Mark Ebbutt, Chepstow (GB); John Bishop, Chepstow (GB); Richard Craven, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 920 days.

(21) Appl. No.: 16/967,060

(22) PCT Filed: Apr. 30, 2019

(86) PCT No.: PCT/EP2019/061056
§ 371 (c)(1),
(2) Date: Aug. 3, 2020

(87) PCT Pub. No.: WO2019/211276
PCT Pub. Date: Nov. 7, 2019

(65) Prior Publication Data
US 2021/0045796 A1 Feb. 18, 2021

(30) Foreign Application Priority Data
May 1, 2018 (GB) ...................................... 1807114

(51) Int. Cl.
*A61B 18/04* (2006.01)
*A61B 18/14* (2006.01)
(Continued)

(52) U.S. Cl.
CPC ........ *A61B 18/042* (2013.01); *A61B 18/1492* (2013.01); *A61B 34/30* (2016.02);
(Continued)

(58) Field of Classification Search
CPC ... A61B 18/042; A61B 18/1492; A61B 34/30; A61B 2017/00323; A61B 2018/00083;
(Continued)

(56) References Cited

U.S. PATENT DOCUMENTS

2005/0149012 A1* 7/2005 Penny .................. A61B 18/042
606/49
2014/0276784 A1 9/2014 Ward et al.
(Continued)

FOREIGN PATENT DOCUMENTS

GB 2520197 A 5/2015
GB 2521611 A 7/2015
(Continued)

OTHER PUBLICATIONS

International Preliminary Report on Patentability issued from the International Preliminary Examining Authority in counterpart International Application No. PCT/EP2019/061056, dated Jun. 3, 2020.
(Continued)

*Primary Examiner* — Jason E Flick
(74) *Attorney, Agent, or Firm* — ArentFox Schiff LLP

(57) ABSTRACT

A treatment apparatus which uses thermal or non-thermal plasma to treat urinary tract infections (UTIs) by destroying bacteria. The apparatus comprises an elongate probe that includes a coaxial cable for conveying radiofrequency (RF) electromagnetic (EM) energy and/or microwave EM energy, a probe tip connected at the distal end of the coaxial cable for receiving the RF and/or microwave EM energy, and a gas conduit for conveying gas to the probe tip. The probe tip comprises a first electrode connected to the inner conductor
(Continued)

of the coaxial cable, and a second electrode connected to the outer conductor of the coaxial cable, and wherein the first electrode and second electrode are arranged to produce an electric field from the received RF and/or microwave EM energy across a flow path of gas received from the gas conduit to produce a thermal or a non-thermal plasma.

15 Claims, 4 Drawing Sheets

(51) Int. Cl.
| | |
|---|---|
| *A61B 34/30* | (2016.01) |
| *A61L 2/00* | (2006.01) |
| *A61L 2/26* | (2006.01) |
| *H05H 1/46* | (2006.01) |
| *A61B 17/00* | (2006.01) |
| *A61B 18/00* | (2006.01) |
| *A61B 18/18* | (2006.01) |
| *A61B 90/00* | (2016.01) |

(52) U.S. Cl.
CPC .............. *A61L 2/0011* (2013.01); *A61L 2/26* (2013.01); *H05H 1/46* (2013.01); *A61B 2017/00323* (2013.01); *A61B 2018/00083* (2013.01); *A61B 2018/00505* (2013.01); *A61B 2018/00642* (2013.01); *A61B 2018/00821* (2013.01); *A61B 2018/00982* (2013.01); *A61B 2018/1435* (2013.01); *A61B 2018/1861* (2013.01); *A61B 2034/303* (2016.02); *A61B 2090/376* (2016.02); *A61L 2202/11* (2013.01); *H05H 1/4645* (2021.05); *H05H 2245/32* (2021.05)

(58) Field of Classification Search
CPC ........... A61B 2018/00505; A61B 2018/00642; A61B 2018/00821; A61B 2018/00982; A61B 2018/1435; A61B 2018/1861; A61B 2034/303; A61B 2018/00583; A61B 2018/00791; A61B 2018/1846; A61B 2034/301; A61B 2017/00092; A61B 2018/00517; A61B 2018/00702; A61B 18/1815; A61B 18/00; A61B 18/14; A61B 2017/00318; A61B 2017/003; A61L 2/0011; A61L 2/26; A61L 2202/11; A61L 2/14; A61L 2/0005; A61L 2/0023; A61L 2/0029; A61L 2/0064; A61L 2/12; H05H 1/46; H05H 1/4645; H05H 2245/32; H05H 1/4637; H05H 1/00; H05H 1/24; H05H 1/461; H05H 2245/00; H05H 2245/30; H05H 2245/36; A61M 2210/1085; A61M 2210/1089; A61M 2210/1092; A61M 2210/1078; A61M 2210/1096
See application file for complete search history.

(56) References Cited

U.S. PATENT DOCUMENTS

| | | | |
|---|---|---|---|
| 2016/0113700 A1* | 4/2016 | Hancock | .................. A61N 1/40 606/29 |
| 2016/0361558 A1 | 12/2016 | Jacofsky et al. | |
| 2017/0354453 A1* | 12/2017 | Krasik | ................. A61B 18/042 |

FOREIGN PATENT DOCUMENTS

| | | |
|---|---|---|
| GB | 2547941 A | 9/2017 |
| GB | 2554181 A | 3/2018 |
| JP | 2006-181353 A | 7/2006 |
| JP | 2017-050267 A | 3/2017 |
| WO | WO 2009/060213 A1 | 5/2009 |
| WO | WO 2014/184544 A1 | 11/2014 |
| WO | WO 2019/175063 A1 | 9/2019 |

OTHER PUBLICATIONS

International Search Report and Written Opinion, issued by International Searching Authority in corresponding International Application No. PCT/EP2019/061056, dated Jul. 29, 2019.
Search Report under Section 17(5), issued by the United Kingdom Intellectual Property Office in counterpart United Kingdom Application No. GB1807114.2, dated Oct. 15, 2018.
Written Opinion of the International Preliminary Examining Authority, issued by the International Preliminary Examining Authority in corresponding International Application No. PCT/EP2019/061056, dated Apr. 7, 2020.

* cited by examiner

APPARATUS FOR TREATING URINARY TRACT INFECTIONS

CROSS-REFERENCE TO RELATED APPLICATIONS

This application is a National Stage entry of International Application No. PCT/EP2019/061056, filed on Apr. 30, 2019, which claims priority to British Patent Application No. 1807114.2, filed on May 1, 2018. The disclosures of the priority applications are hereby incorporated in their entirety by reference.

TECHNICAL FIELD

The invention relates to an apparatus suitable for use in treating urinary tract infections (UTIs).

BACKGROUND TO THE INVENTION

Urinary tract infections (UTIs) are a common type of infection and can affect many areas within the urinary tract. As shown in FIG. 2, the urinary tract 50 includes kidneys 52a, 52b; ureters 54a, 54b; bladder 56 and urethra 58. UTIs can cause pain and discomfort, and so quick treatment is desirable.

The infections can be caused by a number of different bacteria, though the most common cause is *Escherichia coli* (*E. coli*). The conventional treatment for UTIs is therefore antibiotics. However, in addition to side effects of such treatment, antibiotics can be slow to take effect, and in some cases can require multiple courses of antibiotics. Furthermore, antibiotics are becoming less effective for treating UTIs due to the growth in types of antibiotic-resistant bacteria. Slow or ineffective treatment may be particularly harmful where the infection spreads to a patient's kidneys, which can have more serious symptoms and require invasive treatment.

An improved treatment for UTIs, without the use of antibiotics, is therefore highly desirable.

SUMMARY OF THE INVENTION

At its most general, the present invention provides a treatment apparatus which uses thermal or non-thermal plasma to treat urinary tract infections (UTIs) by destroying bacteria.

In a first aspect, there is provided an apparatus for treating UTIs, the apparatus comprising: an elongate probe comprising a coaxial cable for conveying radiofrequency (RF) electromagnetic (EM) energy and/or microwave EM energy, a probe tip connected at the distal end of the coaxial cable for receiving the RF and/or microwave EM energy, and a gas conduit for conveying gas to the probe tip; wherein the coaxial cable comprises an inner conductor, an outer conductor and a dielectric material separating the inner conductor from the outer conductor, wherein the probe tip comprises a first electrode connected to the inner conductor of the coaxial cable, and a second electrode connected to the outer conductor of the coaxial cable, and wherein the first electrode and second electrode are arranged to produce an electric field from the received RF and/or microwave EM energy across a flow path of gas received from the gas conduit to produce a thermal or a non-thermal plasma.

The apparatus thereby allows UTIs to be treated without the use of antibiotics. Treatment using an apparatus according to the invention is quick and effective, reducing discomfort for a patient due to symptoms of a UTI which would otherwise persist during the course of conventional treatment with antibiotics.

The use of thermal or non-thermal plasma provides a reduction in bioburden for a range of bacteria or fungi associated with UTIs, including *E. coli*, *Klebsiella pneumoniae*, and *Staphylococcus aureus*, among others. The apparatus may also be configured to produce a combination of non-thermal plasma and non-ionising microwave radiation. Preferably, the device is configured to produce a non-thermal plasma, having a temperature of less than 41° C., such as 37° C. or less. In this way the apparatus is able to provide a reduction in bioburden and treat a UTI while avoiding damage to surrounding tissue.

In some embodiments it may be preferable to control a duty cycle of RF and/or microwave frequency energy which is delivered to the probe tip. A gas flow rate may also be adjustable, for example the gas flow rate may be adjustable between 1.5 and 10 litres per minute. In this way the apparatus may be configured to allow a physician to control or adjust the number of microbes (e.g. bacteria or fungi) which are eliminated by the treatment apparatus. This may be useful to help a physician ensure that an infection is properly treated without adversely affecting a patient's microbiota (flora or microflora), the microorganisms which reside on or within human tissues including in the urinary tract.

The apparatus may be dimensioned to fit a urethra and/or ureter of a patient, such that the probe tip may have a diameter of less than 10 mm, e.g. 3 mm or less. In some embodiments, the apparatus is dimensioned to fit an instrument channel of a scoping device, such as a laparoscope or the like, which may be used to introduce the elongate probe to a patient's urinary tract, either directly or via a small incision.

The elongate probe preferably comprises a biocompatible coating. For example, the coaxial cable and gas conduit may comprise a polyether block amide (PEBAX) coating and the probe tip may comprise a silver coating. Other biocompatible materials may also be considered. The elongate probe may be introduced into the urinary tract of a patient as a standalone apparatus, or may be introduced through a surgical scoping device.

Preferably, the elongate probe may be steerable to help a physician position the probe tip correctly during treatment. For example, the probe tip may be steerable by control or steering wires, e.g. pull/push rods or the like, which run from a proximal end to a distal end of the elongate probe. The elongate probe is preferably flexible along its length, but in some embodiments it may have a greater flexibility towards its distal end in order to assist with steering of the probe tip by control wires.

In some embodiments the coaxial cable may have a lumen extending from a proximal end to a distal end thereof. This may be used to house control wires which may steer the probe tip through the urinary tract of a patient, or in other embodiments it may form the gas conduit.

In some embodiments the elongate probe may further comprise an optical channel, e.g. for transmitting light to illuminate and/or capture images of a treatment site at the distal end of the elongate probe. This may help a physician locate the region of the urinary tract to be treated. Where the elongate probe is introduced to the patient through a scoping device, the scoping device may comprise an optical channel for transmitting light to illuminate and/or capture images of the treatment site. Additionally or alternatively, the scope may be detectable by fluoroscopy or other imaging techniques such that a physician can locate and track the device within a patient's urinary tract during treatment.

Optionally, the apparatus may further comprise a withdrawal device which is configured to automatically withdraw the elongate probe from a patient's urinary tract at a predetermined rate. The withdrawal device may comprise a cable coupling element operably connected to the elongate probe at a proximal end thereof, and a motor arranged to drive the cable coupling element to cause relative movement between the elongate probe and a patient's urinary tract in a longitudinal direction. For example, the withdrawal device may comprise a motor, optionally a stepper motor, arranged to drive one or more wheels or rollers which engage a portion of the elongate probe (e.g. the coaxial cable) so as to move the elongate probe in a proximal direction such that the elongate probe may be withdrawn from a urinary tract. For example, the motor may be adjustable or configured such that the withdrawal rate is less than 10 mm/sec, or less than 5 mm/sec, such as 1 mm/sec or less. The predetermined withdrawal speed is set by the speed of the motor, which may be set and adjusted by a physician.

The apparatus of the present invention may form part of a robotically assisted surgical system which may be controlled by a physician directly or through computer control.

The second electrode may enclose an internal volume of the probe tip, wherein the first electrode may extend longitudinally within the internal volume, and wherein the probe tip may further comprises an insulating cap mounted at a distal end of the coaxial cable to isolate the coaxial cable from the internal volume. In such embodiments, the gas conduit is in fluid communication with the internal volume via a flow path formed between the insulating cap and the second electrode, wherein the first electrode and second electrode are configured to receive the RF and/or microwave energy from the coaxial cable to set up an electric field in the internal volume for striking a plasma therein, and wherein the probe tip includes an outlet for releasing plasma from the internal volume. Such an arrangement makes plasma production very efficient, reducing treatment time and ensuring that bacteria are eliminated to such an extent that the infection does not flare up again after treatment.

The insulating cap may be mounted within the second electrode, e.g. to define a proximal end of the internal volume. The flow path may comprise a plurality of openings in the second electrode that permit gas flow around the insulating cap. The plurality of openings may be regularly space to facilitate a uniform flow of gas into the internal volume.

The insulating cap may help to ensure that plasma is generated in a distal part of the probe tip, and may also help to direct generated plasma out of the probe tip. In some embodiments, the insulating cap may have a chamfered distal end in the region of an opening through the second electrode. This may help to increase velocity of gas along the flow path the second electrode, aiding throughput of gas and direction of plasma out of the distal end of the probe tip.

The second electrode may be a cylinder. The plurality of openings may each comprise a longitudinal notch in the cylinder. For example, a proximal end of the second electrode may be castellated to provide the plurality of openings.

The elongate probe may comprise a protective sleeve that defines a lumen through which the coaxial cable extends. The gas conduit may be a passageway formed between an outer surface of the coaxial cable and an inner surface of the protective sleeve. This can also ensure that the apparatus is compact for easy insertion through a patient's urinary tract.

The probe tip may comprise a conductive cap mounted on the first electrode at a distal end of the internal volume. The conductive cap is isolated from the second conductor. For example, the conductive cap may be spaced from a distal end of the second electrode to define the outlet. The conductive cap may ensure that plasma is efficiently produced and helps to direct plasma circumferentially from the end of the probe tip to effectively destroy bacteria within a treatment region, in particular where the infection affects the side wall of a patient's urethra or ureters. The conductive cap effectively acts as an extension of the first electrode for generation of plasma.

The first electrode may be helical. A helical electrode advantageously provides series resonance in the electrode at the microwave frequency, thereby delivering maximum energy into the gas and plasma. The first electrode is formed from a portion of the inner conductor of the coaxial cable that extends beyond a distal end of the outer conductor.

The gas conduit may have an input port located at a proximal end of the elongate probe for connecting to a source of gas (e.g. a pressurised gas canister or the like). The gas which is supplied may be any one of: air, helium, argon, nitrogen and carbon dioxide. In some embodiments, gas mixtures may be used. The apparatus may include a flow controller arranged to adjustably control gas flow in the gas conduit. For example the gas flow rate may be adjustable between 1.5 and 10 litres per minute. The gas flow rate may affect the size of the plasma plume or the plasma energy; this may be controlled by the flow controller.

In some embodiments the probe tip may include sensing means to provide information concerning the plasma to enable adjustments (if needed) to take place, e.g. spectral content, plasma energy and plasma temperature. For example, the plasma applicator may include a temperature sensor and/or one or more photodetectors. The information obtained from these sensors may be used in a feedback loop to control the plasma produced, e.g. control the microwave power level, the duty cycle, the waveform of the microwave power, the gas flow rate, the gas mixture, the gas timing etc.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate probe. In use the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz, and most preferably 400 kHz. The microwave frequency may be adjusted to enable the microwave energy delivered to be optimised. For example, a probe tip may be designed to operate at a certain frequency (e.g. 900 MHz), but in use the most efficient frequency may be different (e.g. 866 MHz).

BRIEF DESCRIPTION OF THE DRAWINGS

An embodiment of the invention is discussed below in more detail with reference to the accompanying drawings, in which.

DETAILED DESCRIPTION; FURTHER OPTIONS AND PREFERENCES

Figure 1:
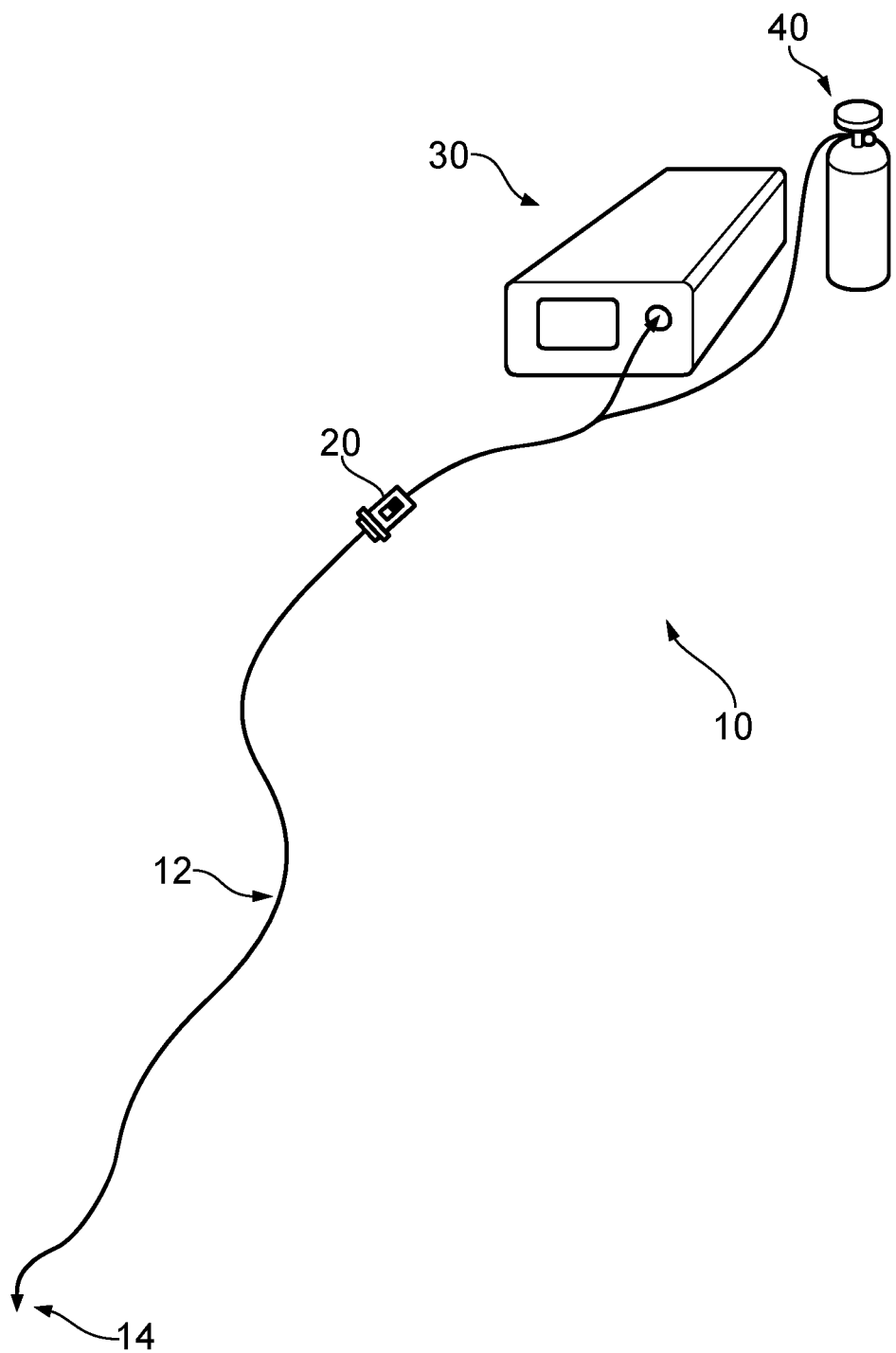
FIG. 1 shows a treatment apparatus that is an embodiment of the invention.

FIG. 1 shows a treatment apparatus 10 that is an embodiment of the invention. The treatment apparatus comprises an elongate probe, e.g. having the form of a flexible shaft. The elongate probe comprises a coaxial cable 12 having a probe tip 14 at its distal end. The elongate probe may include a protective sleeve, for example made of PEBAX, in which the coaxial cable 12 is conveyed, but this is not essential. A generator 20 is connected to a proximal end of the coaxial cable 12. A gas supply 30 is also connected to the elongate probe to supply gas to the probe tip 14 through a gas conduit (not shown) that extends through the elongate probe. The gas conduit may form part of the coaxial cable 12, e.g. may be a longitudinal hollow passageway formed within the coaxial cable, e.g. within its inner conductor. Alternatively, the gas conduit may be a separate tube or passageway extending alongside the coaxial cable, e.g. within the protective sleeve. The gas supply 30 may be a supply of any suitably inert gas for formation of a non-thermal or thermal plasma, e.g. argon, helium, nitrogen, carbon dioxide or a combination thereof. The gas supply 30 may be configured to allow adjustment of the flow rate of gas which is delivered to the distal end of the elongate probe. The gas supply 30 can supply between 1.5 and 10 litres of gas per minute, for example.

In some examples, it may also be desirable to supply ultraviolet (UV) light through the elongate probe, e.g. via an optic fibre, to assist in the treatment process. An optic fibre may also be used to illuminate and/or capture images of a treatment site at the distal end of the elongate probe.

During a treatment process, with the probe tip 14 positioned within a patient's urinary tract, the generator 20 supplies radiofrequency (RF) electromagnetic (EM) energy and/or microwave EM energy to the probe tip 14. The gas supply 30 simultaneously supplies gas to the probe tip 14 via the gas conduit. The RF and/or microwave energy and supplied gas are combined at the probe tip 14 to generate a thermal or non-thermal plasma, which is emitted from the probe tip 14 to contact a surface of the urinary tract to destroy or eliminate micro-organisms. Examples of plasma generation in this manner are disclosed in WO 2009/060213 A1, for example.

The generator may be controlled to determine whether the generated plasma is a non-thermal or thermal plasma. For example, the supply microwave energy may have a power and/or duty cycle that is selectable to produce non-thermal or thermal plasma. Preferably, the generator is operated to produce a non-thermal plasma having a temperature of less than 41° C., which can help avoid long term damage to tissue in the treatment site.

The apparatus 10 may further include a withdrawal device (not shown) coupled to the coaxial cable 12 and operable to withdraw the coaxial cable 12 through a patient's urinary tract at a predetermined rate.

Figure 2:
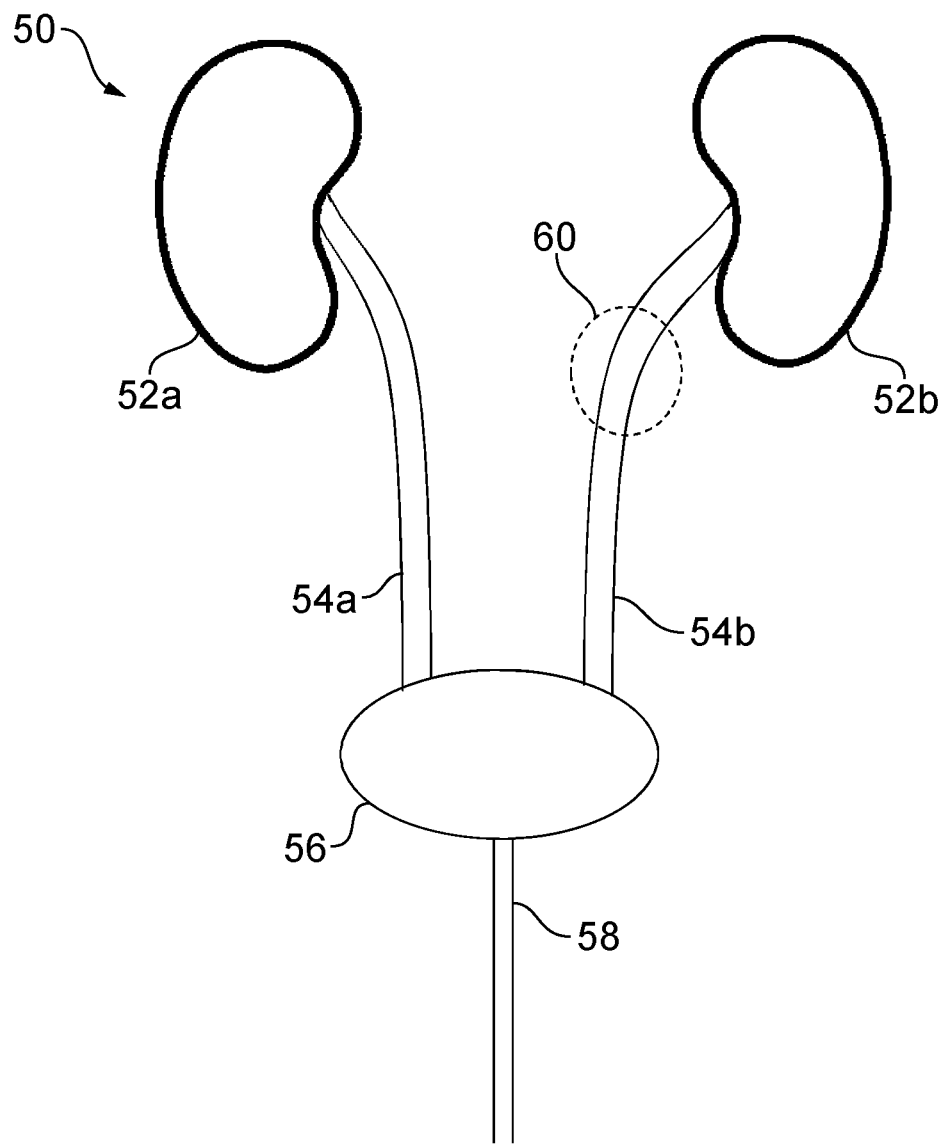
FIG. 2 is a schematic view of a human urinary tract in which the invention can be used to treat infections.

FIG. 2 shows a schematic view of a urinary tract 50. The urinary tract comprises kidneys 52*a*, 52*b*, ureters 54*a*, 54*b*, bladder 56 and urethra 58. A urinary tract infection (UTI) can affect any of these parts of the human anatomy. For example, a UTI may occur in a region 60 of a ureter 54*b*. Antibiotics are typically used to treat UTIs, but these may be ineffective or slow. The present invention provides an apparatus which allows an improved method of treatment of an infection in any part of the urinary tract 50.

To treat the infection 60, the probe tip 14 is advanced through the urethra 58 and bladder 56 and steered by a physician to enter the correct ureter 54*b*. For example, the probe tip 14 may be steerable by control wires which run from a proximal end to a distal end of the elongate probe. When the probe tip 14 is advanced enough to be located in region 60, the generator 20 is operated to deliver RF and/or microwave frequency EM energy to the probe tip 14, and the gas supply 30 simultaneously conveys gas through the gas conduit to the probe tip 14. The physician may be aided in guiding the probe tip 14 to the treatment region 60 by images received from the distal end of the elongate probe and/or other device imaging techniques such as fluoroscopy. In this way, a thermal or non-thermal plasma can be generated within the infected region 60 to destroy bacteria or other micro-organisms responsible for the UTI.

The device may then be withdrawn from the urinary tract 50 manually by the physician, or a separate withdrawal device may be used. The withdrawal device may have one or more rollers driven by a motor, such that when the withdrawal device connected to the coaxial cable the motor is operable to automatically withdraw the elongate probe from the urinary tract 50 at a rate of around 1 mm/sec.

It is also envisaged that the probe tip 14 may be advanced to the treatment site 60 through a surgical scoping device, such as a laparoscope or the like. The scoping device may be passed through the urethra 58 and bladder 26 to ureter 54*b*. Alternatively, the scoping device may be passed through an incision in the patient's abdomen to access treatment site 60 directly, without passing through the urinary tract 50.

Figure 3:
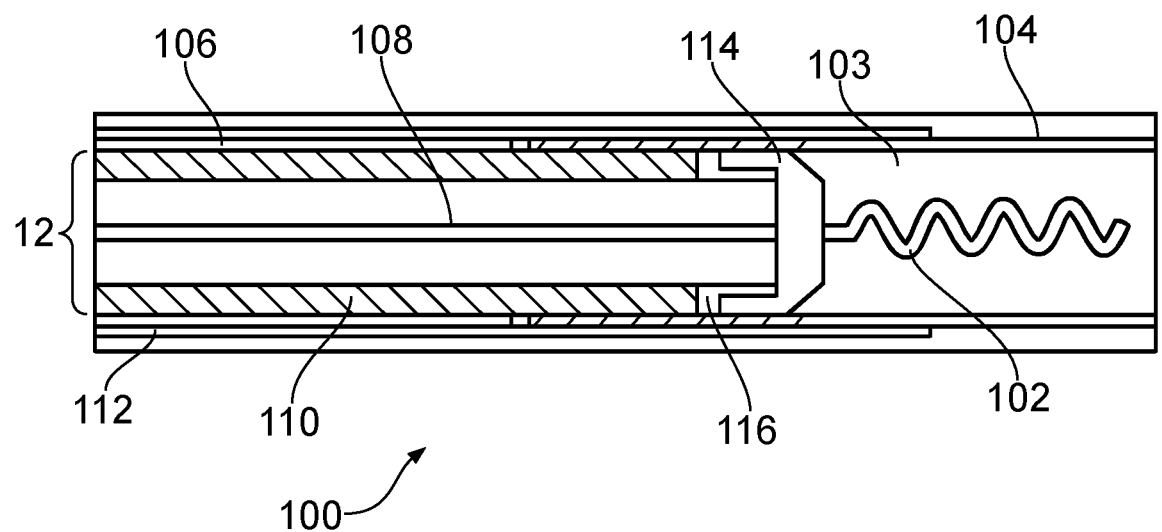
FIG. 3 shows a cross-section view of a first probe tip for use with the present invention.

FIG. 3 shows a cross section view of a first probe tip 100 for use in the present invention, e.g. for use in the apparatus 10 discussed above. Probe tip 100 can be connected to the distal end of a coaxial cable 12 as shown in FIG. 1. The probe tip 100 is configured to receive RF and/or microwave EM energy and gas in order to produce a thermal or non-thermal plasma which can be directed out of the distal end of the probe tip 100 towards an infection site within the urinary tract of a patient.

In this embodiment, the probe tip 100 comprises a first electrode 102 and a second electrode 104 at a distal end thereof. The first electrode 102 has a helical shape and the second electrode 104 is a hollow cylinder which is open at each end, wherein the first electrode 102 is positioned generally along the longitudinal axis of the second electrode 104. A space 103 (also referred to as a plasma generating region) is thereby defined between the first electrode 102 and the second electrode 104. Each of the first electrode 102 and the second electrode 104 may comprise a biocompatible coating such as silver.

Figure 4:
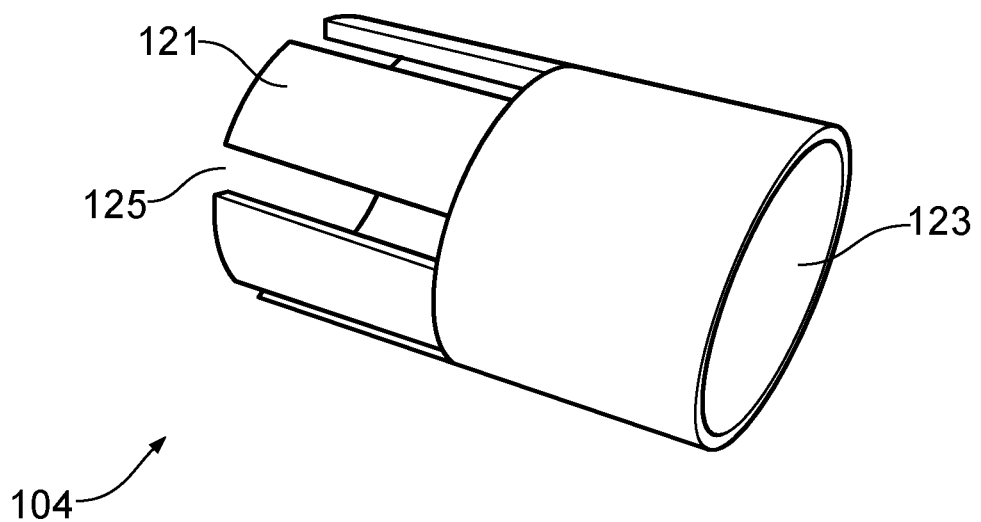
FIG. 4 is a perspective view of a second electrode which is used with the first probe tip.

The second electrode 104 has castellations (i.e. a series of protruding fingers 121 separated by notches 125 as shown in FIG. 4) formed in a proximal end. The castellations permit gas to flow from an annular gas conduit 106 surrounding coaxial cable 12 into the space within the second electrode 104. A plasma may be struck by configuring the supplied RF and/or microwave EM radiation to generate a high electric field between the first electrode 102 and the second electrode 104 in the space 103. The plasma may be struck using RF EM energy, and sustained by the microwave EM energy. The generated plasma flows out of the distal open end of the second electrode 104 to contact a surface of the patient's urinary tract in which the elongate probe is inserted.

The coaxial cable 12 comprises an inner conductor 108 separated from an outer conductor 110 by an insulating dielectric material 111. The first electrode 102 is connected to an inner conductor 108 of the coaxial cable and the second electrode 104 is connected to an outer conductor 110 of the coaxial cable 12. In some embodiments, the first electrode 102 may additionally comprise a cap at its distal end, such as a cap 218 shown in FIG. 5 and discussed below.

The gas conduit 106 may be formed by an annular gap between an outer surface of the outer conductor 110 of the coaxial cable and a protective sleeve 112 which surrounds the coaxial cable 12. As discussed above, gas can be introduced to the gas conduit 106 at or around the proximal end of the coaxial cable 12 from a gas supply 30.

The second electrode 104 is configured to fit over the outer conductor 110 and within the sleeve 112 at the distal end of the coaxial cable 12. The second electrode 104 therefore sits within the gas conduit 106 at its distal end. Gas is able to flow from the gas conduit 106 to within the second electrode 104 through the castellations which are formed in the proximal end of the second electrode 104.

Within the second electrode 104, positioned at the distal end of the coaxial cable 12, is a generally cylindrical ceramic cap 114. The ceramic cap 114 is spaced away from a distal end of the outer conductor 110 of the coaxial cable 12. A longitudinal gap 116 between these parts may be filled with an adhesive, e.g. a UV-curing adhesive, to prevent any arcing between the outer conductor 110 and the inner conductor 108.

The ceramic cap 114 may extend for around 2 mm in the longitudinal direction. The ceramic cap 114 has a chamfered distal end face to encourage gas flowing from the gas conduit 106 into the space 103 to pass between the first electrode 102 and second electrode 104, where the plasma is struck. The first electrode 102 is connected to the inner conductor 108 of the coaxial cable by a conductive element (not shown) that extends through the ceramic cap 114. The conductive element may be a portion of the inner conductor 108 that protrudes beyond the distal end of the outer conductor 110.

The first electrode 102 of this embodiment is formed from a wire which is twisted to form a helical or spiral structure. The wire in some embodiments may be wound around a solid core of a dielectric material, e.g. PTFE, PEEK or a ceramic material. Alternatively, the wire may be wound around a thin-walled open cylinder. The wire may preferably made from a good conductor such as copper, silver, gold or plated steel to ensure that conductor losses are minimised in the probe tip 100. The wire may be a distal portion of the inner conductor 108 that extends out of a distal end of the coaxial cable 12.

The first electrode 102 is configured to be a resonant structure at the microwave frequencies used with the present invention. At these frequencies, the wire forming the first electrode 102 displays inductive behaviour. By forming the first electrode 102 as a helix, there is a capacitance created between each adjacent turn when energy is supplied to the tip 100. This structure therefore creates appropriate conditions for series resonance in the first electrode 102, having a minimum impedance at the microwave frequency of EM energy supplied to the probe tip 100.

FIG. 4 shows a perspective view of an example of the second electrode 104. The second electrode 104 is a hollow cylinder having an open distal end 123 to allow plasma produced within the electrode to flow out of the distal end. The proximal end of the electrode 104 is also open, such that the electrode can be fitted to the distal end of a coaxial cable in a manner as described above. The proximal end of the electrode 104 is castellated such that a plurality of notches 125 are formed between fingers 121 in the proximal end of the electrode 104. These notches 125 allow gas to flow to the interior of the electrode 104 from a gas conduit 106, as described above, where the gas is struck to create a thermal or non-thermal plasma. It may be desirable to have a plurality of notches spaced regularly around the circumference of the second electrode 104 so that the flow of gas into the space 103 is substantially uniform relative around the longitudinal axis.

The second electrode 104 has a total length of at least 11 mm, where the distance between the base of the castellations and the distal end of the second electrode 104 is at least 3 mm, preferably at least 5 mm. For example, the distance may be 6.8 mm. This distance is generally equivalent to the length of the volume within the second electrode 104 in which the thermal or non-thermal plasma is generated.

Figure 5:
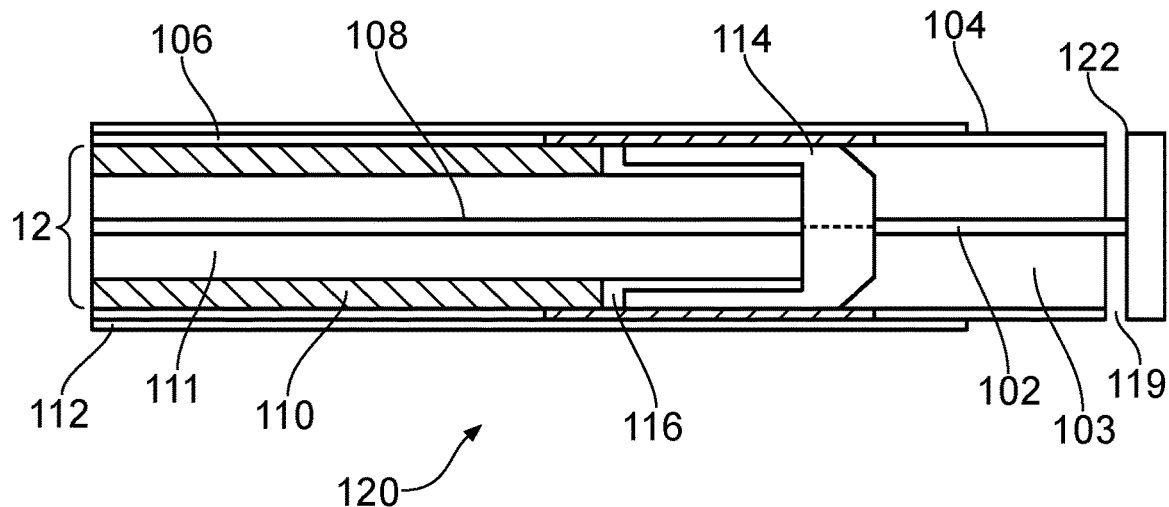
FIG. 5 shows a cross-section view of a second probe tip for use with the present invention.

FIG. 5 shows a cross section view of a second embodiment of a probe tip 120 for use with the present invention. Features of the second probe tip 120 which correspond with the first probe tip 100 have been given the same reference numerals, and are not described again. The probe tip 120 is fitted at the distal end of a coaxial cable in a similar manner as the first probe tip 100 described above.

In the probe tip 120, the first electrode 102 is straight rather than helical. For example, the first electrode 102 may simply be an extension of the inner conductor 108 of the coaxial cable. At the distal end of the first electrode 102 is a conductive end cap 122, which is spaced away from the distal end of the second electrode 104 to define a gap 119. The probe tip 120 is configured to receive RF and/or microwave EM energy and gas in order to produce a thermal or non-thermal plasma. The probe tip 120 operates in a similar manner as probe tip 100 described above.

The end cap 122 assists in maintaining the thermal or non-thermal plasma and also operates to direct the plasma towards an infected region of a urinary tract to destroy bacteria and other microorganisms when the probe tip 120 is positioned within the patient's urinary tract. The end cap 122 may be a circular disc, e.g. having a diameter similar to (preferably slightly greater than) an outer diameter of the second electrode 104. The end cap 122 is made of a conductive material such as copper, silver, gold or plated steel. The end cap 122 is connected to the distal end of the first electrode 102 such that there is a gap of around 0.5 mm between the distal end of the second electrode 104 and the end cap 122. An end cap may also be used in embodiments having a helical first electrode, such as probe tip 100 shown in FIG. 2.

In a development of the arrangement shown in FIG. 5, a temperature sensor, e.g. a thermocouple or a plurality of thermocouples, may be arranged in the proximity of the plasma generating region. For example, a thermocouple may be mounted at a distal end of the protective sleeve 112. Signals to and from the thermocouple may be conveying within the sleeve or gas conduit 106.

The temperature sensor is arranged to detect a temperature at the plasma generating region and send a signal back to the controller that is indicative of the temperature. The controller may then be arranged to control the instrument to prevent the plasma from becoming a thermal plasma.

In use, the instrument will be in close proximity to the inner wall of the urethra. It is therefore important that the temperature is limited to around 40° C. so that it cannot damage the organ. The signal from the temperature sensor may be used in a closed loop control circuit in the controller (generator) to control plasma generation parameters. For example, the control circuit may operate to control any one or more of: (i) the microwave power level of the sustain pulses, (ii) the ON time and/or OFF time of the pulses of microwave energy, (iii) the duration of the burst of RF voltage, (iv) the overall treatment time, (v) the applicator feed speed, and (vi) the flow rate of the gas. Alternatively, the generator may be arranged to cut off the energy delivery upon detecting that a threshold temperature is reached.

Providing a temperature sensor may ensure the instrument is operated within a safe temperature region.

Figure 6:
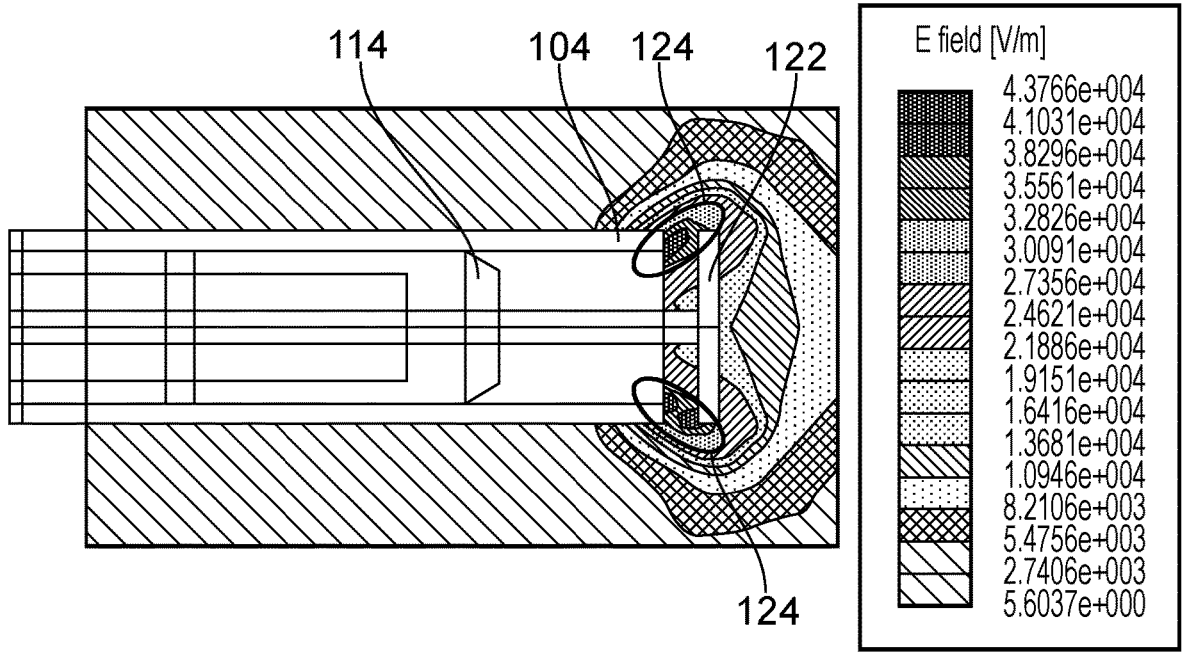
FIG. 6 is a computer simulated model showing the location of plasma generated by the second probe tip.

FIG. 6 is a computer-generated simulation showing electric field strength around the probe tip 120 when in use. It can be seen that the presence of the end cap 122 acts to concentrate the electric field in an annular region 124 that extends between a distal end of the second electrode 104 and a longitudinally opposed portion of the end cap 122. This indicates that plasma can be generated in this region, whereupon the flow of gas through the space 103 will be deflected by the end cap 122. This may be particularly useful to direct thermal or non-thermal plasma to sidewalls of a urethra 58 or ureters 54a, 54b for treatment of an infection in those areas.

The invention claimed is:

1. A urinary tract infection treatment apparatus comprising:
   an elongate probe comprising a coaxial cable for conveying radiofrequency (RF) electromagnetic (EM) energy or microwave EM energy,
   a probe tip connected at the distal end of the coaxial cable for receiving the RF or microwave EM energy, and
   a gas conduit for conveying gas to the probe tip;
   wherein the coaxial cable comprises an inner conductor, an outer conductor and a dielectric material separating the inner conductor from the outer conductor,
   wherein the probe tip comprises a first electrode connected to the inner conductor of the coaxial cable, and a second electrode connected to the outer conductor of the coaxial cable,
   wherein the first electrode and second electrode are arranged to produce an electric field from the received RF or microwave EM energy across a flow path of gas received from the gas conduit to produce a non-thermal plasma,
   wherein the second electrode encloses an internal volume of the probe tip, wherein the first electrode extends longitudinally within the internal volume,
   wherein the probe tip further comprises an insulating cap mounted at a distal end of the coaxial cable to isolate the coaxial cable from the internal volume,
   wherein the gas conduit is in fluid communication with the internal volume via a flow path formed between the insulating cap and the second electrode,
   wherein the first electrode and second electrode are configured to receive the RF or microwave energy from the coaxial cable to set up an electric field in the internal volume for striking a plasma therein,
   wherein the probe tip includes an outlet for releasing plasma from the internal volume,
   wherein the probe tip comprises a conductive cap mounted on the first electrode at a distal end of the internal volume, the conductive cap being spaced from a distal end of the second electrode to define the outlet, and
   wherein the elongate probe comprises a biocompatible coating.

2. The apparatus of claim 1, wherein the elongate probe further comprises steering wires for steering the probe tip.

3. The apparatus of claim 1, further comprising a withdrawal device mountable on the elongate probe and configured to retract the elongate probe therethrough.

4. The apparatus of claim 1, further comprising a surgical scoping device for introducing the elongate probe to a urinary tract.

5. The apparatus of claim 4, wherein the surgical scoping device is a flexible scoping device.

6. The apparatus of claim 1, wherein the insulating cap is mounted within the second electrode, and wherein the flow path comprises a plurality of openings in the second electrode that permit gas flow around the insulating cap.

7. The apparatus of claim 6, wherein the second electrode is a cylinder, and the plurality of openings each comprise a longitudinal notch in the cylinder.

8. The apparatus of claim 6, wherein a proximal end of the second electrode is castellated to provide the plurality of openings.

9. The apparatus of claim 1, wherein the elongate probe comprises a protective sleeve that defines a lumen through which the coaxial cable extends, and wherein the gas conduit is a passageway formed between an outer surface of the coaxial cable and an inner surface of the protective sleeve.

10. The apparatus of claim 1, wherein the first electrode is helical.

11. The apparatus of claim 1, wherein the first electrode is formed from a portion of the inner conductor of the coaxial cable that extends beyond a distal end of the outer conductor.

12. The apparatus of claim 1, wherein the insulating cap has a chamfered distal edge.

13. The apparatus of claim 1, wherein the apparatus is part of a robotically assisted surgical system.

14. The apparatus of claim 1, wherein the probe tip includes a temperature sensor arranged to detect a temperature of the plasma.

15. The apparatus of claim 14, further comprising a controller configured to control plasma generation parameters of the plasma based on a signal from the temperature sensor.

* * * * *